United States Patent
Ledger et al.

(10) Patent No.: US 6,324,424 B1
(45) Date of Patent: Nov. 27, 2001

(54) REDUCTION OF SKIN IRRITATION DURING ELECTROTRANSPORT DELIVERY

(75) Inventors: Philip W. Ledger, Carlton (GB); Michel J. N. Cormier, Mountain View; Patricia S. Campbell, Palo Alto, both of CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/105,074

(22) Filed: Jun. 26, 1998

Related U.S. Application Data

(62) Division of application No. 08/895,096, filed on Jul. 16, 1997, now Pat. No. 5,865,792, which is a continuation of application No. 08/608,582, filed on Feb. 28, 1996, now Pat. No. 5,693,010, which is a continuation of application No. 08/221,123, filed on Mar. 30, 1994, now abandoned.

(51) Int. Cl.⁷ .................................................. A61N 1/30
(52) U.S. Cl. .................................... 604/20; 424/449
(58) Field of Search ................ 604/20, 501; 424/78.02, 424/449, 78.05

(56) References Cited

U.S. PATENT DOCUMENTS

| | | | |
|---|---|---|---|
| 4,211,222 | 7/1980 | Tapper | 128/207.21 |
| 4,343,798 | 8/1982 | Fawzi | 424/240 |
| 4,406,658 * | 9/1983 | Latlin et al. | 604/20 |
| 4,608,249 | 8/1986 | Otsuka et al. | 424/28 |
| 4,640,689 * | 2/1987 | Sibalis | 604/20 |
| 4,666,441 | 5/1987 | Andriola et al. | 604/897 |
| 4,744,787 * | 5/1988 | Phipps et al. | 604/20 |
| 4,752,285 | 6/1988 | Petelenz et al. | 604/20 |
| 4,885,154 | 12/1989 | Cormier et al. | 424/10 |
| 4,927,408 * | 5/1990 | Haak et al. | 604/20 |
| 4,990,340 * | 2/1991 | Hidaka et al. | 424/449 |
| 5,000,956 | 3/1991 | Amkraut et al. | 424/434 |
| 5,047,007 * | 9/1991 | McNichols et al. | 604/20 |
| 5,049,387 | 9/1991 | Amkraut | 424/435 |
| 5,068,226 * | 11/1991 | Weinshenker et al. | 604/20 |
| 5,077,054 | 12/1991 | Amkraut et al. | 424/486 |
| 5,084,006 * | 1/1992 | Lew et al. | 604/20 |

(List continued on next page.)

FOREIGN PATENT DOCUMENTS

| | | | |
|---|---|---|---|
| 0314528 | 3/1989 | (EP) | A61L/15/03 |
| 0547482 | 6/1993 | (EP) | A61N/1/30 |
| 6023312 | 2/1985 | (JP) | A61K/9/70 |
| WO8809175 | 12/1988 | (WO) | A61K/31/58 |
| WO9217239 | 10/1992 | (WO) | A61N/1/30 |

OTHER PUBLICATIONS

Yoshida et al., Advanced Drug Delivery Reviews, 9 (1992) pp 239–264; Structure–Transport Relationships in Transdermal Iontophoresis.

Ledger, Philip W., Advanced Drug Delivery Reviews, 9 (1992) pp 289–307; Skin Biological Issues in Electrically Enhanced Transdermal Delivery.

Burrows, William M., Stoughton, Richard B., Arch Dermatol– vol. 112, Feb. 1976, pp 175–178; "Inhibition of Induction of Human Contact Sensitization by Topical Glucocorticosteroids".

Rapperport, S. "Adjunctive Uses for Iontophoresis", Fifth International Congress of Plastic and Reconstructive Surgery, pp 797–802, Ed. J.T. Hueston, Butterworths, Australia, 1971.

*Primary Examiner*—Mark Bockelman
(74) *Attorney, Agent, or Firm*—D. Byron Miller; Owens J. Bates

(57) ABSTRACT

The invention is directed to a composition and product for use in an electrotransport device. The composition includes an ionized drug, an anti-inflammatory agent and a solvent. Preferably, the anti-inflammatory agent is hydrocortisone or esters thereof, and the solvent is water and a material such as an alcohol, a glycol, a glycerol, a cyclodextrin, a nonionic surfactant and/or mixtures thereof.

23 Claims, 6 Drawing Sheets

U.S. PATENT DOCUMENTS

| | | | |
|---|---|---|---|
| 5,118,509 | 6/1992 | Amraut | 424/449 |
| 5,120,545 | 6/1992 | Ledger et al. | 424/449 |
| 5,130,139 | 7/1992 | Cormier et al. | 424/450 |
| 5,149,539 | 9/1992 | Ledger et al. | 424/449 |
| 5,160,741 | 11/1992 | Cormier et al. | 424/450 |
| 5,169,382 * | 12/1992 | Theeuwes et al. | 604/20 |
| 5,171,576 | 12/1992 | Amkraut et al. | 424/449 |
| 5,215,520 * | 6/1993 | Shroot et al. | 604/20 |
| 5,221,254 * | 6/1993 | Phipps | 604/20 |
| 5,232,441 | 8/1993 | Stephen et al. | 604/49 |
| 5,334,138 * | 8/1994 | Sage, Jr. et al. | 604/20 |
| 5,464,387 | 11/1995 | Haak et al. | 604/20 |
| 5,874,095 * | 2/1999 | Deckner. | |

\* cited by examiner

REDUCTION OF SKIN IRRITATION DURING ELECTROTRANSPORT DELIVERY

This is a division of U.S. patent application Ser. No. 08/895,096 filed on Jul. 16, 1997, now U.S. Pat. No. 5,865,792 which is a continuation of U.S. patent application Ser. No. 08/608,582 filed on Feb. 28, 1996, now U.S. Pat. No. 5,693,010 which is a continuation of U.S. patent application Ser. No. 08/221,123 filed on Mar. 30, 1994 abandoned.

TECHNICAL FIELD

This invention relates to electrotransport agent delivery devices, compositions, and methods. More particularly, this invention relates to methods of reducing skin irritation during transdermal electrotransport agent delivery.

BACKGROUND ART

The term "electrotransport" as used herein refers generally to the delivery of an agent (eg, a drug) through a membrane, such as skin, mucous membrane, or nails, which delivery is induced by application of an electrical potential. For example, a beneficial therapeutic agent may be introduced into the systemic circulation of a human body by electrotransport delivery through the skin. A widely used electrotransport process, iontophoresis, involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field, through which pores an agent can be delivered either passively (ie, without electrical assistance) or actively (ie, under the influence of an electric potential). However, in any given electrotransport process, more than one of these processes may be occurring simultaneously to a certain extent.

Accordingly, "electrotransport", as used herein, should be given its broadest possible interpretation so that it includes the electrically induced or enhanced transport of at least one agent, which may be charged, uncharged, or a mixture thereof, regardless of the specific mechanism or mechanisms by which the agent actually is transported.

Electrotransport devices generally use at least two electrodes which are in electrical contact with some portion of the skin, nails, mucous membrane, or other surface of the body. One electrode, commonly referred to as the "donor" or "active" electrode, is the electrode from which the agent is delivered into the body. The other electrode, typically termed the "counter" or "return" electrode, serves to close the electrical circuit through the body. For example, if the agent to be delivered is positively charged, ie a cation, then the anode will be the active or donor electrode, while the cathode serves to complete the circuit. Alternatively, if an agent is negatively charged, ie an anion, the cathode will be the donor electrode. Additionally, both the anode and cathode may be considered donor electrodes if both anionic and cationic agent ions are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is connected to the donor electrode, while the opposite pole is connected to the counter electrode. In addition, some electrotransport devices have an electrical controller which controls the current applied through the electrodes, thereby regulating the rate of agent delivery. Furthermore, passive flux control membranes, adhesives for maintaining device contact with a body surface, insulating members, and impermeable backing members are some other potential components of electrotransport devices.

Although the advantages of electrotransport delivery are numerous (eg, enhanced transmembrane flux of beneficial agents compared to passive, ie, non-electrically assisted flux; precise control of agent delivery, including patterned delivery, etc.), there are disadvantages under certain application conditions. One potential problem with electrotransport transdermal delivery is skin irritation. For instance, applying an electric current through skin under certain conditions has been known to cause skin irritation. See for example, "Skin Biological Issues in Electrically Enhanced Transdermal Delivery", P. Ledger, Advanced Drug Delivery Reviews, Vol. 9 (1992), pp 289–307.

The prior art has recognized that the pH of the solution of the drug or agent being delivered (ie, the pH of the donor reservoir in an electrotransport device) can have an effect on skin irritation. According to "Structure-Transport Relationships in Transdermal Iontophoresis" by Yoshida et al, *Ad. Drug Del. Rev.* (1992), 9, 239–264, the preferred pH range of the donor reservoir, for avoiding skin irritation is 3 to 8. Outside this pH range, according to this reference, irritation and/or damage of the stratum corneum can occur. Furthermore, previous disclosures relating to minimizing skin irritation from electrotransport devices have concentrated on the active or donor reservoir. However, electrotransport devices apply as much current through the counter electrode as through the donor electrode, and hence, skin irritation, erythema and/or damage due solely to application of electric current also occurs beneath the counter reservoir or counter electrode. In a typical electrotransport device, the area of device/skin contact beneath the counter reservoir is nearly equivalent to the area beneath the donor reservoir. Hence, skin erythema, irritation, and/or damage in the counter reservoir contact area may be similar in magnitude to that in the donor reservoir contact area.

DISCLOSURE OF THE INVENTION

Hence, it is an object of this invention to provide an apparatus and method by which tissue irritation may be reduced or eliminated during and after electrotransport of an agent through a body surface (eg, skin).

A further object of this invention is to improve patient compliance with electrotransport drug administration schedules by reducing or preventing skin irritation caused by transdermal electrotransport drug delivery.

Satisfaction of these objects and other advantages of this invention will become apparent from the electrotransport device and method of the present invention. The electrotransport device contains donor and counter reservoirs which are adapted to be placed in ion-transmitting relation with a body surface such as the skin or a mucosal membrane of an animal. The donor reservoir contains the drug to be delivered. The device includes a source of electrical power which can apply a voltage across the donor and counter reservoirs in order to apply a predetermined level of electric current therethrough and through said body surface. At least one of the reservoirs contains a solution of an anti-inflammatory agent selected from the group consisting of hydrocortisone, an ester of hydrocortisone and salts thereof. The flux of the anti-inflammatory agent is sufficient to reduce body surface irritation associated with said applied level of electric current. The flux of the anti-inflammatory agent necessary to reduce tissue irritation encountered with electrotransport drug delivery is typically in the range of about 0.03 to 10 $\mu g/cm^2 \cdot h$, and preferably in the range of about 0.1 to 5 $\mu g/cm^2 \cdot h$.

Preferably, the anti-inflammatory agent is hydrocortisone, hydrocortisone phosphate and/or hydrocortisone succinate, most preferably hydrocortisone. When the anti-inflammatory agent is hydrocortisone, the reservoir which contains the hydrocortisone preferably contains a liquid solvent selected from the group consisting of an alcohol, a glycerol, a glycol, a cyclodextrin, and an aqueous solution of a surfactant.

In another embodiment of the present invention, a method of reducing body surface (eg, skin) irritation during (eg, transdermal) electrotransport delivery of a drug is presented. The method involves placing the donor and counter reservoirs of an electrotransport delivery device in ion-transmitting relation with a body surface, the donor reservoir containing the drug to be delivered. An anti-inflammatory agent is placed in at least one of said donor and counter reservoirs. The anti-inflammatory agent is selected from the group consisting of hydrocortisone, esters of hydrocortisone and salts thereof. The method also includes applying an electrical potential across the donor and counter reservoirs in order to generate an applied level of electric current through the body surface and deliver the drug through the body surface by electrotransport. The anti-inflammatory agent is delivered to the body surface at a flux which is sufficient to reduce body surface irritation associated with the applied level of electric current and the electrotransport drug delivery. The flux of the anti-inflammatory agent necessary to reduce tissue irritation and encountered with electrotransport drug delivery is typically in the range of about 0.03 to 10 $\mu g/cm^2 \cdot h$, and preferably in the range of about 0.1 to 5 $\mu g/cm^2 \cdot h$.

Preferably, the anti-inflammatory agent is hydrocortisone, hydrocortisone phosphate and/or hydrocortisone succinate, most preferably, hydrocortisone. When the anti-inflammatory agent is hydrocortisone, the reservoir which contains the hydrocortisone preferably contains a liquid solvent selected from the group consisting of an alcohol, a glycerol, a glycol, a cyclodextrin, and an aqueous solution of a surfactant.

The preferred anti-inflammatory agent, hydrocortisone, when in solution is an uncharged (ie, electrically neutral, being neither a cation nor an anion) species. Accordingly, the hydrocortisone is delivered through the body surface by the combination of passive diffusion and electroosmosis, rather than electromigration. The electroosmotic flux of hydrocortisone, like other unchanged species, is greater from the anodic reservoir than from the cathodic reservoir. The electroosmotic flux of hydrocortisone is dependent upon a number of factors including the concentration of the species in solution, the pH and ionic strength of the solution, the current density and the polarization of the electrode. The necessary concentration of hydrocortisone in order to achieve sufficient reduction or elimination of body surface irritation will be dependent upon whether the hydrocortisone is contained in an anodic reservoir or a cathodic reservoir In general, the flux of hydrocortisone from either reservoir should be about 0.03 to 10 $\mu g/cm^2 \cdot h$ and preferably about 0.1 to 5 $\mu g/cm^2 \cdot h$.

BRIEF DESCRIPTION OF THE DRAWINGS

This invention will be described in further detail with reference to the accompanying drawings wherein.

MODES FOR CARRYING OUT THE INVENTION

As used herein, the term "irritation" refers to the inflammatory reaction of body tissues, especially skin, caused by one or more stimulus including, but not limited to, application of electric current to the tissue, delivery of an irritating substance (eg, an irritating drug) into the tissue, pH changes in the tissue due to electrotransport delivery, occlusion of the tissue by an electrotransport device and/or bacterial overgrowth in the tissue caused by occlusion and friction between the electrotransport device and the tissue. In the case of skin, irritation is generally evidenced by an inflammatory response exhibiting redness or erythema.

The term "irritation" as used herein does not refer to sensitization which is a two-phase process involving an induction phase followed by an elicitation phase. The induction phase occurs when the body is exposed to the sensitizing agent and during this phase no adverse reaction to the agent is manifested. The length of time for the induction phase to occur varies widely. Some agents such as poison ivy, for example, will complete the induction phase within a very short time after the initial exposure. Other agents may require repeated or continuous exposure over periods of weeks or months before the induction phase is completed. Whatever period of time is involved, no adverse body surface (eg, skin or mucosal membrane) reaction will be elicited until after the induction phase has occurred. Thereafter, the next exposure to the sensitizing agent will elicit an allergic response (called elicitation) commonly manifested by burning, itching, reddening and/or blistering of the skin or mucosa usually at the site of application but often at the site of previous exposure or even elsewhere on the body.

Figure 1:
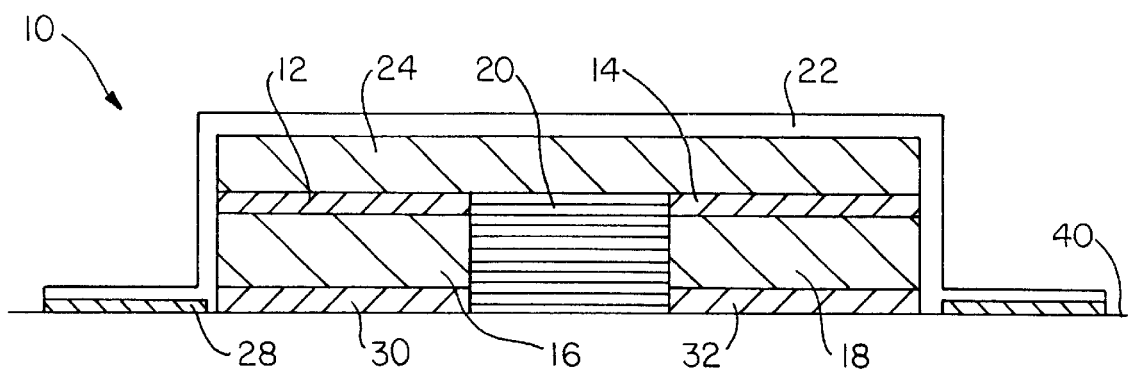
FIG. 1 is a sectional view of one embodiment of an electrotransport device useful in accordance with the present invention.

The present invention may be utilized in a wide variety of electrotransport devices. In general, electrotransport devices have a source of electrical power (eg, one or more batteries) which is, or may be, electrically connected to a donor electrode including a reservoir capable of holding a liquid solution or suspension of the agent to be delivered and a counter electrode including a liquid solution or suspension of an electrolyte salt. One example of an electrotransport device 10 is illustrated in FIG. 1. Device 10 has two electrodes, comprised of electrically conductive materials, referred to herein as a donor electrode 12 and a counter electrode 14. The donor and counter electrodes 12 and 14 are positioned adjacent to, and in electrical contact with, the donor reservoir 16 and the counter reservoir 18, respectively. The donor reservoir 16 contains the agent to be delivered, while the counter reservoir 18 may contain a biocompatible electrolytic salt or another agent to be delivered. An electrical insulator 20 is positioned between (i) the donor electrode 12 and donor reservoir 16 and (ii) the counter electrode 14 and counter reservoir 18. Insulator 20, which may be an air gap or may be composed of a material which conducts neither electrons nor ions. Insulator 20 prevents device 10 from short-circuiting through a path which does not include the body surface 40 to which device 10 is applied. The device 10 optionally includes a backing layer 22 composed of a liquid impermeable non-conducting material. Device 10 has an electronic circuit, illustrated schematically in FIG. 1 as layer 24, having a DC power source (eg, one or more batteries) therein. Typically, the electronic circuit layer 24 is relatively thin and preferably comprised of electronically conductive pathways printed, painted or otherwise deposited on a thin, flexible substrate such as, for example, a film or polymeric sheet, eg, the electronic circuit layer 24 is a printed flexible circuit. In addition to the power source, the electronic circuit layer 24 may also include one or more electronic components which control the level, waveform shape, polarity, timing, etc. of the electric current applied by device 10. For example, circuit layer 24 may contain one or more of the following electronic components: control circuitry such as a current controller (eg, a resistor or a transistor-based current control circuit), an on/off switch, and/or a microprocessor adapted to control the current output of the power source over time. The magnitude of the applied electrotransport current density (current density equals the applied current ($\mu$A) divided by the skin contact area ($cm^2$) of the anodic or cathodic electrode/reservoir) is typically in the range of about 10 to 250 $\mu A/cm^2$, more typically in the range of about 50 to 150 $\mu A/cm^2$. The outputs of circuit layer 24 are electrically connected to the electrodes 12 and 14 most typically in a manner such that each electrode is in electrical contact with an opposite pole of the power source within circuit layer 24. The device adheres to the body surface in this embodiment by means of a peripheral adhesive layer 28. Optionally, the device may contain an in-line adhesive layer, ie, an adhesive applied to the body surface-contacting faces of reservoirs 16, 18 or applied to the body surface-contacting faces of membranes 30, 32. An in-line adhesive must be composed of an agent-transmitting material, ie, the agent being delivered must be capable of penetrating the adhesive layer to reach the body surface 40. Optional flux control membranes 30 and 32 are positioned between donor reservoir 16 and body surface 40 and between counter reservoir 18 and body surface 40, respectively, in order to limit or control the amount of passive (ie, not electrically assisted) flux of agent to body surface 40.

The device 10 of FIG. 1 is merely one example of an electrotransport device useful in accordance with present invention. The present invention is useful in a wide variety of electrotransport devices, including those devices which are not unitary, ie those which have a desk-top power supply unit and two remote electrode assemblies which are attached to the patient and connected to the power supply unit by long (eg, 1 to 2 m) electrically conductive wires or cables. An example of a non-unitary electrotransport device having remote electrodes appears in Petelenz et al, U.S. Pat. No. 4,752,285 (See FIG. 6), which is incorporated herein by reference. In addition, the device 10 may contain other features, such as a removable release liner (not shown) on the adhesive layer 28 and/or the body surface-contacting face of the device. Furthermore, certain components in device 10 are unnecessary or optional for practicing the instant invention. For example, if electrodes 12 and 14 are chosen such that a galvanic couple exists, an independent power source in circuit layer 24 may be an optional component. Thus, device 10 of FIG. 1 is presented solely for illustration of one embodiment of an electrotransport device which can be utilized to practice the present invention.

If the agent to be delivered is anionic, ie, negatively charged, the cathodic electrode is the donor electrode and the cathodic reservoir is the donor reservoir, containing the agent, and the anodic reservoir is the counter reservoir, containing a biocompatible electrolytic salt. Alternatively, if the agent to be delivered is cationic, ie positively charged, the anodic electrode is the "donor" electrode and the anodic reservoir is the donor reservoir containing the agent to be delivered and the cathodic reservoir is the counter reservoir.

At least one of the donor and counter reservoirs contains a solution of an anti-inflammatory agent selected from the group consisting of hydrocortisone, esters of hydrocortisone and salts thereof. Preferably, the anti-inflammatory agent is selected from hydrocortisone, hydrocortisone phosphate, hydrocortisone succinate, and mixtures thereof. Most preferred is hydrocortisone (ie, 11,17,21-trihydroxypregn-4-ene-3,20-dione). One important advantage of hydrocortisone is that prolonged exposure does not result in unacceptable local side effects such as skin thinning, and it is approved for over-the-counter use at concentrations up to 10 mg/mL.

In general, electrotransport devices utilize at least two reservoirs (ie, an anodic reservoir and a cathodic reservoir) which are adapted to be placed in ion-transmitting relation with a body surface, such as intact skin, at spaced apart locations. In accordance with the present invention, at least one of these reservoirs contains a solution of the anti-inflammatory agent in a concentration which induces an electrotransport and/or passive diffusion flux of the anti-inflammatory agent into the body surface which is sufficient to reduce or prevent irritation caused by either the application of electric current, the delivery of an irritating drug or other substance in the skin, or both. Most preferably, the solution of the anti-inflammatory agent is contained in the donor reservoir, and most preferably in an anodic donor reservoir.

The transdermal flux of anti-inflammatory agent which is typically required to reduce and/or eliminate skin irritation is generally in the range of about 0.03 to 10 $\mu g/cm^2 \cdot h$, and more preferably in the range of about 0.1 to 5 $\mu g/cm^2 \cdot h$.

Those skilled in the art of transdermal electrotransport drug delivery will appreciate that a number of factors will affect the transdermal electrotransport flux of an anti-inflammatory agent, including the concentration of the anti-inflammatory agent in solution, the polarity of the electrode, the pH and and the ionic strength of the solution, the level of applied electric current, the area of reservoir skin contact and other factors. However, the hydrocortisone/ester flux rates may be determined by measuring the hydrocortisone concentration in the blood plasma using standard analytical techniques, and from these the flux rates are easily calculated.

Typically, electrotransport drug delivery devices use donor and counter electrodes which contain aqueous solutions of drug or electrolyte salts. Water is a preferred solvent since it is completely biocompatible and is non-irritating to the skin. However, the water solubility of hydrocortisone is poor, generally less than 0.3 mg/mL. Thus when using hydrocortisone as the anti-inflammatory agent, the liquid solvent used in the reservoir preferably comprises an aqueous solution of a material selected from the group consisting of an alcohol, a glycerol, a glycol, a cyclodextrin and a surfactant. Specific examples of such aqueous solutions include aqueous solutions of alcohols such as ethanol, propanol and isopropanol; aqueous solutions of glycerols; aqueous solutions of glycols such as propylene glycol and polyethylene glycols; aqueous solutions of cyclodextrins such as $\alpha$, $\beta$ or $\gamma$ cyclodextrins as well as anionic or cationic cydodextrin derivatives; and aqueous solutions of non-ionic surfactants including polyoxyethylenes such as TWEEN® 20 (chemical name: polyoxyethylene(20) sorbitan monolaurate), TWEEN® 40 (chemical name: polyoxyethylene(20) sorbitan monopalmitate), TRITON® X-100 and TRITON® X-114; aqueous solutions of alkyldimethylamine oxides, such as dodecyidimethylamine oxide, at pH above 6; aqueous solutions of alkyl glucosides, such as decyl-$\beta$-D-glucopyranoside, nonyl-$\beta$-D-glucopyranoside, octyl-$\beta$-D-glucopyranoside, heptyl-$\beta$-D-glucopyranoside, hexyl-$\beta$-D-glucopyranoside; aqueous solutions of alkyl maltosides, such as dodecyl-$\beta$-D-maltoside and decyl-$\beta$-D-maltoside; alkyl thioglucosides, such as octyl-$\beta$-D-thioglucopyranoside and heptyl-$\beta$-D-thioglucopyranoside; aqueous solutions of Big CHAP series species, such as deoxyBigCHAP and BigCHAP; aqueous solutions of glucamides; and mixtures thereof. Preferred are aqueous solutions of the non-ionic surfactants TWEEN® 20 and TWEEN® 40.

Preferably, the concentration of the anti-inflammatory agent in the donor and/or counter reservoir solution is in the range of about 0.1 to 50 mg/ml, more preferably about 3 to 10 mg/ml.

In the case of the most preferred anti-inflammatory agent, hydrocortisone, the agent is uncharged in solution. Hence, the transdermal flux of hydrocortisone is due to the combination of (1) passive diffusion; and (2) electroosmotic flux of the hydrocortisone into the body surface. The electroosmotic flux of electrically neutral species such as hydrocortisone is significantly higher from the anodic reservoir than from the cathodic reservoir, other conditions such as concentration, pH and ionic strength of the solution, and applied level of current being equal. In general, at neutral pH the electroosmotic flux of an electrically neutral species from an anodic reservoir is about 2–10 times higher than the electroosmotic flux of the same species from the cathodic reservoir. Those skilled in the art will appreciate that the concentration of hydrocortisone which must be placed in an anodic reservoir at neutral pH is therefore much lower than the concentration of hydrocortisone which must be placed in a cathodic reservoir at neutral pH in order to obtain the necessary hydrocortisone flux rates necessary to reduce or prevent irritation.

The addition of an anti-inflammatory agent to a given reservoir affects primarily the skin directly adjacent (eg, in contact with) that reservoir. Thus, the addition of an anti-inflammatory agent to the cathodic reservoir affects the irritation of the skin site adjacent to the cathodic reservoir, while the addition of an anti-inflammatory agent to the anodic reservoir affects the irritation of the skin site adjacent to the anodic reservoir. Accordingly, this invention contemplates those devices in which the anti-inflammatory agent is added to (i) the cathodic reservoir, (ii) the anodic reservoir and (iii) both reservoirs. However, in the preferred practice of the invention, the anti-inflammatory agent is added to both the anodic reservoir and the cathodic reservoir. More preferably, hydrocortisone is added to both the anodic and cathodic reservoirs.

In some instances, it may be difficult or impossible to add an anti-inflammatory agent to the donor reservoir of an electrotransport device, as described herein, in order to reduce the irritation of the body surface site adjacent the donor reservoir. For example, if the drug to be delivered from the electrotransport system is chemically incompatible with (eg, unstable in the presence of) the anti-inflammatory agent or if the level of applied electric current necessary to achieve the desired drug flux is insufficient to produce an irritation-reducing flux of the anti-inflammatory agent, then the application of the present invention to such a donor reservoir may be of little or no benefit. However, even with such an electrotransport system, the present invention may be utilized in the counter reservoir. Thus, the present invention has particular utility when adding the anti-inflammatory agent to the counter reservoir from which no drug is being delivered. Thus, in cases where a cationic drug is being delivered from an anodic reservoir, the present invention is particularly useful in placing the anti-inflammatory agent in the counter cathodic reservoir. Conversely, when delivering an anionic drug from the cathodic reservoir, the present invention is particularly useful in placing the anti-inflammatory agent in the anodic counter reservoir. Even in those cases where the anti-inflammatory agent cannot be added to the donor reservoir, the irritation of the skin which is adjacent the counter reservoir can still be substantially reduced. Thus, at the very least, the present invention provides a method for reducing or eliminating at least about one half of the skin irritation potential (ie, the skin site adjacent the counter electrode reservoir) due to electrotransport drug delivery. Of course, it is most preferred that the anti-inflammatory agent be added to both the donor and counter electrode reservoirs in order to reduce the irritation potential for both the skin site adjacent the counter electrode reservoir and the skin site adjacent the donor electrode reservoir.

By placing a solution of an anti-inflammatory agent in the anodic reservoir, the cathodic reservoir or both reservoirs during electrotransport agent delivery, the skin irritation at the skin site adjacent the reservoir(s) which contain the anti-inflammatory agent is reduced. Reduced skin irritation results in better acceptance of the treatment regimen by the patient. Accordingly, patient compliance with prescribed treatment using the electrotransport device is improved.

The donor reservoir and counter reservoir can be formed of any material adapted to absorb and hold a sufficient quantity of liquid therein in order to permit transport of agent therethrough by electrotransport. For example, gauzes, pads or sponges composed of cotton or other absorbent fabric, both natural and synthetic, may be used. Preferably, the matrices of the reservoirs are composed, at least in part, of hydrophilic polymer material. Hydrophilic polymers are typically preferred because water is the preferred ion transport medium, and hydrophilic polymers have a relatively high equilibrium water content. More preferably, the matrices of the reservoirs are solid polymer matrices composed, at least in part, of an insoluble hydrophilic polymer. Insoluble hydrophilic polymer matrices are preferred for structural reasons over soluble hydrophilic polymers, ie reservoir shape may be more easily retained upon hydration of a hydrophilic polymer matrix composed of a water insoluble polymer compared to a matrix composed of a water soluble polymer or gel.

The matrices can be crosslinked with the agent in place, such as with a silastic matrix, or the polymers can be prefabricated and sorbed with the components from solutions as is the case with cellulose, woven fiber pads and sponges. The reservoirs can alternately be a gel matrix structure, formed similarly to the polymeric matrix structure, wherein the gel is formed of a hydrophilic polymer which is swellable or soluble in water. Such polymers can be blended with the components in any ratio, but preferably represent from a few percent up to about 50 percent by weight of the reservoir. The polymers can be linear or cross-linked. Suitable hydrophilic polymers include copolyesters such as HYTREL (DuPont De Nemours & Co., Wilmington, Del.), polyvinylpyrrolidones, polyvinyl alcohol, polyethylene oxides such as POLYOX (Union Carbide Corp.), CARBOPOL (BF Goodrich of Akron, Ohio), blends of polyoxyethylene or polyethylene glycols with polyacrylic acid such as POLYOX blended with CARBOPOL, polyacrylamide, KLUCEL, cross-linked dextran such as SEPHADEX (Pharmacia Fine Chemicals, AB, Uppsala, Sweden), WATER LOCK (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxyethyl ethacrylate (National Patent Development Corp.), natural gums, chitosan, pectin, starch, guar gum, locust bean gum, and the like, along with blends thereof. This list is merely exemplary of the materials suited for use in this invention. Other suitable hydrophilic polymers can be found in J. R. Scott & W. J. Roff, Handbook of Common Polymers (CRC Press, 1971), which is hereby incorporated by reference.

Optionally, the matrices of the reservoirs may contain a hydrophobic polymer for enhanced structural rigidity or improved bonding characteristics. Preferably the hydrophobic polymer is heat fusible, in order to improve the lamination of the reservoirs to adjacent components, such as an insulating material or a rate-controlling membrane. Suitable hydrophobic polymers for use in the reservoir matrices include, but are not limited to, polyisobutylenes, polyethylene, polypropylene, polyisoprenes and polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched alkyl maleamic acids wherein the alkyl group has 10–24 carbon atoms, glycol diacrylates, and blends thereof. Most of the above-mentioned hydrophobic polymers are heat fusible.

The reservoir matrices may be a polymeric matrix structure formed by blending the desired agent, drug, electrolyte, or other component(s), with an inert polymer by processes such as melt blending, solvent casting, or extrusion. The donor reservoir contains an agent to be delivered, while the counter reservoir may contain an electrolyte, eg a water soluble biocompatible salt, such as sodium chloride. In addition to the delivery agent and electrolyte, the reservoirs may also contain other conventional materials such as water, permeation enhancers, dyes, pigments, inert fillers, and the like.

The electrodes of the present invention are composed of an electrically conductive material such as a metal. For example, the electrodes may be formed from metal foil, metal screen, metal deposited or painted on a suitable backing, calendaring, film evaporation, or by embedding a metal powder in a binder matrix. Examples of suitable metals include silver, zinc, silver chloride, aluminum, platinum, stainless steel, gold, and titanium. For example, the anodic electrode may be composed of silver, while the cathodic electrode may be composed of silver chloride.

Further, if the electrodes are selected from dissimilar materials, a galvanic couple may be formed. A galvanic couple may provide all or at least part of the electrical potential required to operate the device. Exemplary of such a galvanic couple are a pair of electrodes formed from silver and zinc chloride.

Alternatively, the electrodes may be formed of a polymer matrix containing a conductive filler such as a metal powder, powdered graphite, carbon fibers, or other electrically conductive filler material. The polymer-based electrodes may be produced by mixing the conductive filler in a polymer matrix, preferably hydrophobic in order to minimize interaction with any water present in the reservoirs.

Preferably, the electrodes of the present invention are comprised of electrochemically reactive materials, ie, the anode is composed of an electrochemically oxidizable material (eg, silver) and/or the cathode is composed of an electrochemically reducible material (eg, silver chloride).

Electrochemically reactive electrode materials are preferred because their use minimizes water hydrolysis, which results in the production of hydroxyl ($OH^-$) and hydronium ($H^+$) ions, which can alter reservoir pH and also introduces competing ions in the donor reservoir. Hydroxyl or hydronium ions may be transported into the skin causing a high or low, respectively, pH in the skin, thereby causing erythema, irritation, and/or damage. The preferred electrochemically reactive electrodes are the aforementioned silver and silver chloride electrodes.

This invention has utility in connection with the delivery of agents within the broad class deliverable through body surfaces, including skin, mucosa, and nails. The expressions "drug" and "agent" are used interchangeably herein and are intended to have their broadest interpretation as any substance which is delivered to a living organism to produce a desired, usually beneficial, effect. In general, this includes therapeutic agents in all of the major therapeutic areas listed hereafter. However, the expressions "drug" and therapeutic "agent" do not encompass the anti-inflammatory agents which are delivered in accordance with the present invention in order to reduce body surface irritation associated with electrically assisted delivery of a drug or other therapeutic agent. Drugs and therapeutic agents in the major therapeutic areas include but are not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary, anticholinergics, antiulceratives such as ranitidine, sympathomimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as enalapril, benzodiazepine antagonists such as flumazenil, diuretics, vasodilators, including general, coronary, peripheral and cerebral, central nervous system stimulants, cough and cold preparations, decongestants, diagnostics, hormones such as parathyroid hormone, hypnotics, immunosuppressives, muscle relaxants, parasympatholytics, parasympathomimetrics, prostaglandins, proteins, peptides, psychostimulants, sedatives and tranquilizers.

The invention is also useful in the controlled delivery of peptides, polypeptides, proteins and other macromolecules. These macromolecular substances typically have a molecular weight of at least about 300 daltons, and more typically a molecular weight in the range of about 300 to 40,000 daltons. Specific examples of peptides, and proteins and macromolecules in this size range include, without limitation, LHRH, LHRH analogs such as buserelin, gonadorelin, napharelin and leuprolide, GHRH, GHRF, insulin, insulotropin, heparin, calcitonin, octreotide, endorphin, TRH, NT-36 (chemical name: N=[[(s)-4-oxo-2-azetidinyl]carbonyl]-L-histidyl-L-prolinamide), liprecin, pituitary hormones (eg, HGH, HMG, HCG, desmopressin acetate, etc.), follicle luteoids, αANF, growth factors such as growth factor releasing factor (GFRF), βMSH, somatostatin, atrial natriuretic peptide, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagon, hirulog, hyaluronidase, interferon, insulin-like growth factors, interleukin-1, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neuropeptide Y, neurotrophic factors, oligodeoxynudeofides and their analogues such as antisense RNA, antisense DNA and anti-gene nucleic acids, opiate peptides, colony stimulating factors, parathyroid hormone and agonists, parathyroid hormone antagonists, prostaglandin antagonists, pentigetide, protein C, protein S, ramoplanin, renin inhibitors, thymosin alpha-1, thrombolytics, TNF, vaccines, vasopressin antagonist analogs, alpha-1 anti-trypsin (recombinant), and TGF-beta.

Having thus generally described the invention, the following examples will illustrate how the invention may be utilized to accomplish effective transdermal electrotransport agent delivery with reduced skin irritation, erythema and/or damage.

EXAMPLE I

In vivo electrically assisted delivery of metoclopramide HCl (MCP), an anti-emetic prescription drug used in the treatment of gastroesophageal reflux and in the prevention of nausea and vomiting, and which has been identified in these studies as a skin irritating drug, was accomplished using custom built electrotransport systems. MCP is a water soluble drug salt. The systems had an anode (donor) reservoir gel containing a 10% aqueous solution of MCP, a 0.5% aqueous solution of hydrocortisone (HC) and 3% hydroxyethyl cellulose (HEC) to form a gel. The systems had a cathode (counter) reservoir gel containing an 0.1M aqueous solution of a buffering agent (citric acid or L-histidine) to maintain the pH of the counter reservoir gel at about pH 4 and 3% HEC to form a gel. The systems had a silver foil anode and a silver chloride cathode. The reservoir gel (ie, both the anodic and cathodic gels) sizes were each approximately 600 $\mu L$ and had a skin contacting surface area of about 5 cm$^2$. The electrodes were connected to a DC power source which supplied a constant level of electric current of 500 $\mu A$ or 100 $\mu A/cm^2$. As a control, each subject wore a second electrotransport system, identical to that described above except the anodic reservoir contained no HC.

Experiments were performed in vivo on seven Caucasian male volunteers, ages 25 to 39 years. The electrotransport systems were applied to and removed from the upper arms of the subjects. The two reservoirs were generally spaced about 5 to 7.5 cm apart. The application site was wiped with alcohol prior to system application. Each week, each subject wore two electrotransport systems (one system having an anodic reservoir containing HC the other system having an anodic reservoir containing no HC), one system per arm, for four hours. Voltage and current were measured at 0.5, 1, 2, 3, and 4 hours after system application. Blood samples (10 mL) were taken from each of the patients immediately prior to application of the systems (time 0 hrs) and at 0.5, 1, 2, 3, 4, 4.5, 5, 6, 8, and 20 hours after system application. The systems were removed at 4 hours after system application. Plasma concentrations of MCP were determined by a high-performance liquid chromatography. Skin sites were evaluated for skin irritation ($\alpha$) using the Minolta Chroma Meter Model No. CR 200 (sold by Minolta Camera Corp., Ltd. Osaka, Japan) at 1, 4, 24 and 48 hours following system removal. The Minolta Chroma Meter is a portable tristimulus color analyzer which converts all colors within the range of human perception into a numerical code using the L*a*b* color notation system. L* (luminance) expresses brightness on the black-white axis; a*, hue on the red-green axis; and b*, chroma on the yellow-blue axis so that a specific numerical code enables an exact color description of an object. The measurement of skin irritation for these tests is given as $\alpha$, which is defined herein as the difference of the mean a* reading for the electrotransport-treated samples minus the mean a* reading for the untreated samples, ie $\alpha = a^*_{treated} - a^*_{untreated}$. Minolta measurements were made by taking the mean a* value of three readings at adjacent untreated sites and subtracting that value from the mean of three readings taken at the treated site. Since changes in redness intensity were made from the a* reading, only a* values were employed for the purposes of skin site checks following electrode removal. The numerical values for a are generated by the Minolta Chroma Meter and have no particular units. The Minolta Chroma Meter utilizes a numerical range of −60 (green) to +60 (red) for a* hue. Typically, human skin ranges from 0 to 10 on the a* hue scale. An $\alpha$ value of 1 to 2 represents a slight redness or erythema; an $\alpha$ value of 3.5 to 4.5 represents a moderate redness or erythema; and an $\alpha$ value of above 7 represents severe redness or erythema.

Figure 3:
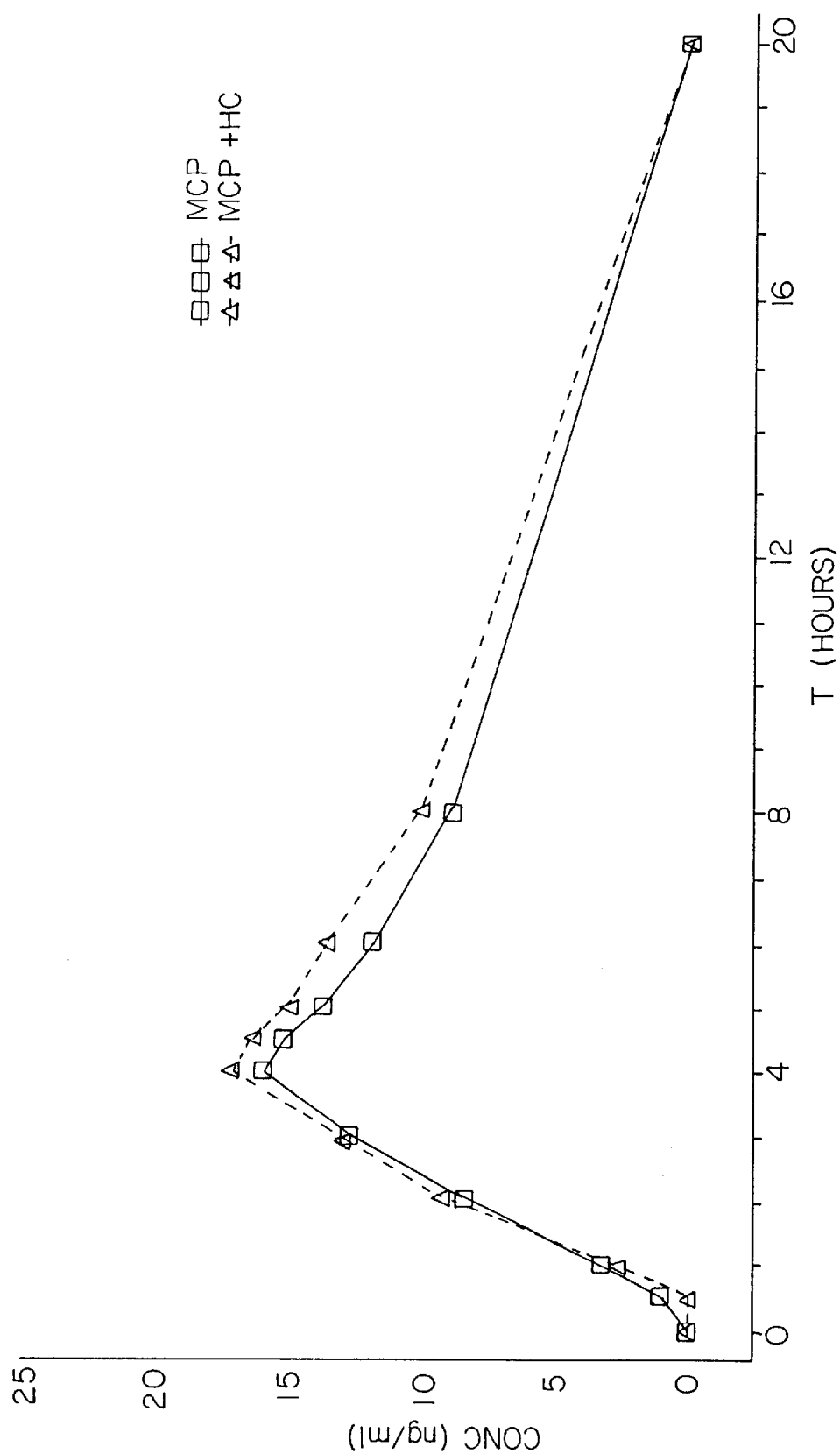
FIG. 3 is a graph of concentration of drug in the blood of the study volunteers as a function of time ($t_w$) during which the electrotransport systems were worn on the skin.

The metoclopramide blood plasma concentrations of the subjects wearing systems which contained only metoclopramide, as well as subjects wearing systems containing metoclopramide and hydrocortisone, are separately plotted in FIG. 3. FIG. 3 clearly shows that the two curves closely approximate one another, indicating that the addition of hydrocortisone into the metoclopramide-containing drug reservoir of the electrotransport system does not significantly affect the delivery of metoclopramide into the bloodstream.

Figure 2:
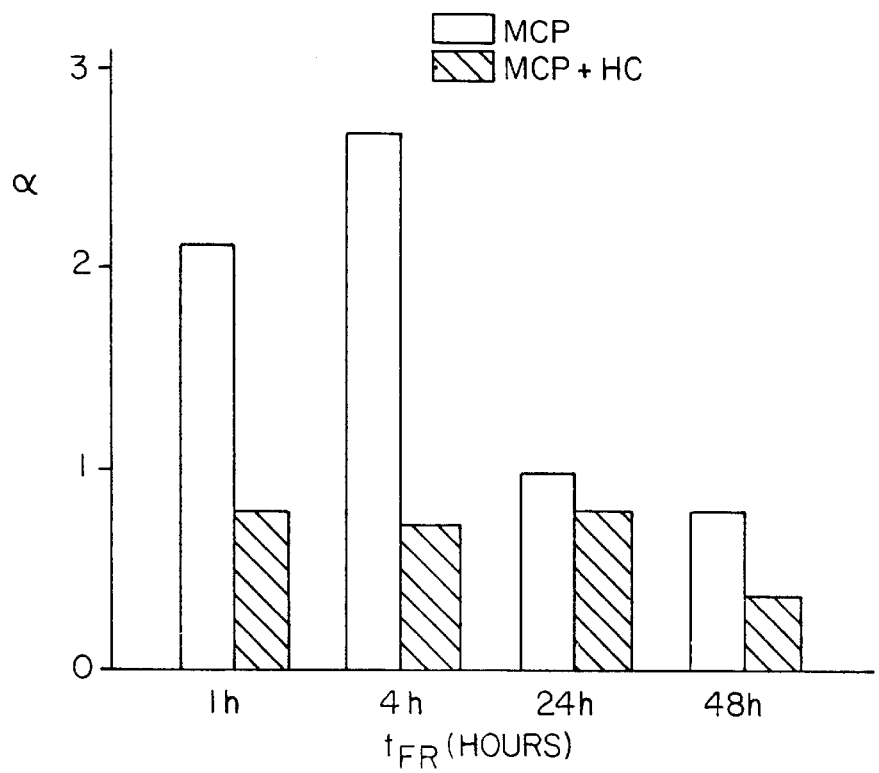
FIG. 2 is a graph of skin irritation ($\alpha$) at the skin site adjacent the anodic (donor) reservoir as a function of time ($t_{FR}$) following removal of the electrotransport systems from the skin.

FIG. 2 illustrates a plot of skin irritation ($\alpha$) versus time following system removal from the skin for the skin sites in contact with the anodic donor reservoirs. As FIG. 2 illustrates, the addition of hydrocortisone to the anodic reservoirs of electrotransport systems resulted in less skin irritation compared to the electrotransport systems having anodic reservoirs containing no hydrocortisone.

EXAMPLE II

These experiments involved the use of hydrocortisone in both the anodic and cathodic reservoirs. The objective of this study was to determine the effect of hydrocortisone (HC) on skin irritation associated with metoclopramide HCl (MCP) electrotransport when added to the anode reservoir (0.05 and 0.50 wt % HC) and the cathode reservoir (0.03% HC) of the electrotransport system.

MCP-containing gels (10% MCP) were prepared for clinical use by mixing MCP and water, adjusting the pH to 7 with 0.5 N NaOH, and then adding hydroxyethylcellulose (HEC, 3%) to the mixture. Gels containing MCP with 0.05 wt % HC and 0.50 wt % HC were prepared by adding the appropriate amount of HC to the MCP solution, adjusting the pH to 7 with 0.5 M NaOH, and adding HEC. MCP-containing gels (with and without HC) were used in the anode reservoirs of the electrotransport systems and pH 7.0 Dulbecco's phosphate buffered saline (PBS) HEC gel, with and without 0.03% HC, was used in the cathode reservoirs. The anode material was silver foil and the cathode material was silver chloride. The applied current levels were the same as in Example I.

Six normal male volunteers between 24 and 37 years of age participated in this study. The electrotransport systems were applied and removed from the backs of the subjects. The application site was wiped with alcohol prior to system application. Each subject wore four different electrotransport systems for eight hours: one system contained MCP with 0.05% HC in the anode reservoir and PBS with 0.03% HC in the cathode reservoir, another system contained MCP with 0.5% HC in the anode reservoir and PBS with 0.03% HC in the cathode reservoir and two systems contained MCP in the anode reservoir and PBS in the cathode reservoir. The two "metoclopramide alone" electrotransport systems were worn to examine the site variability of the skin reaction to MCP in the same subject. For all electrotransport systems the skin-contact area of each gel reservoir was 1.27 cm$^2$ and the applied level of electric current was 127 $\mu$A or 100 $\mu$A/cm$^2$.

Figure 4:
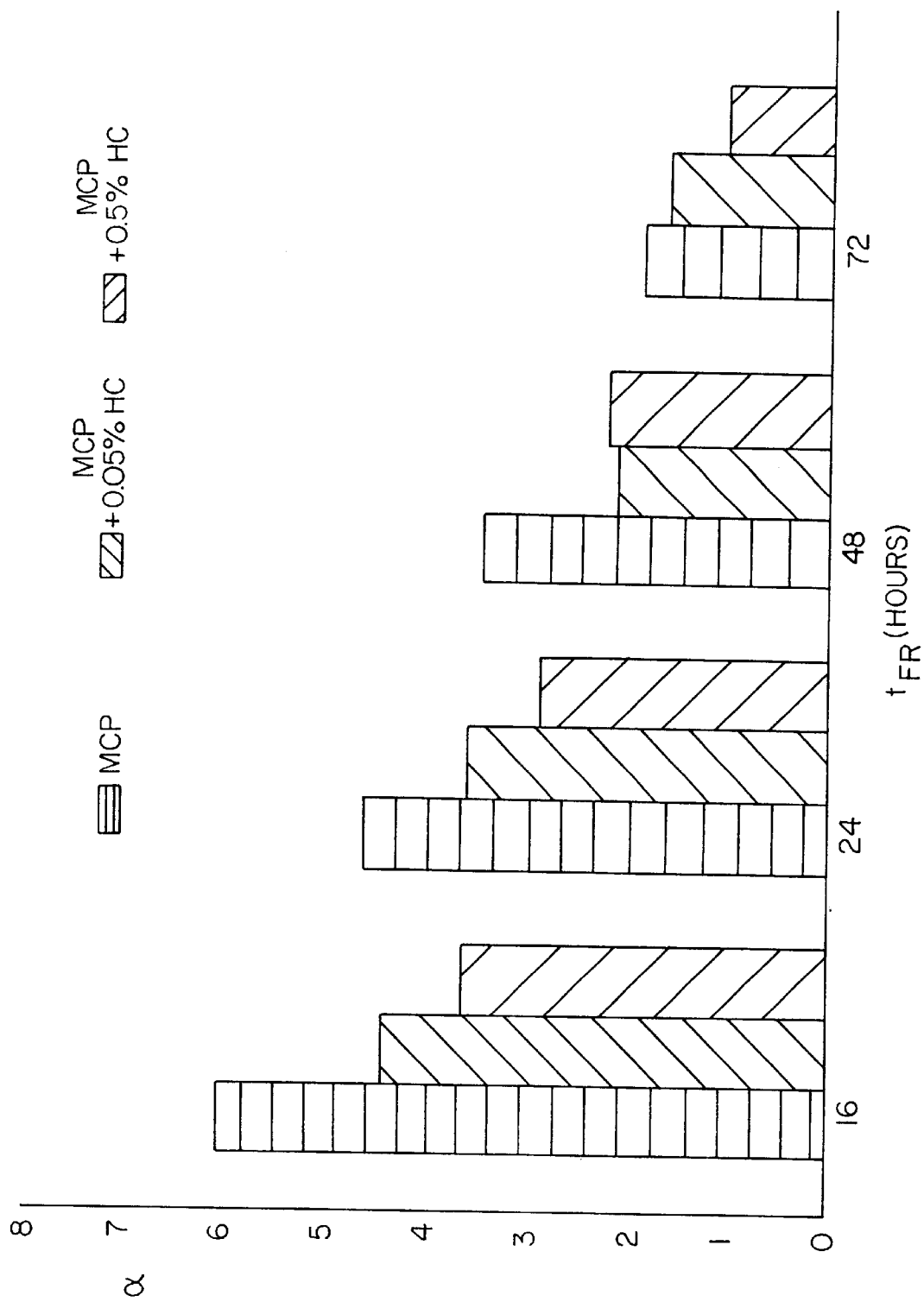
FIG. 4 is a graph of skin irritation ($\alpha$) at the skin site adjacent the anodic (donor) reservoir as a function of time ($t_{FR}$) following removal of the electrotransport systems from the skin.
Figure 5:
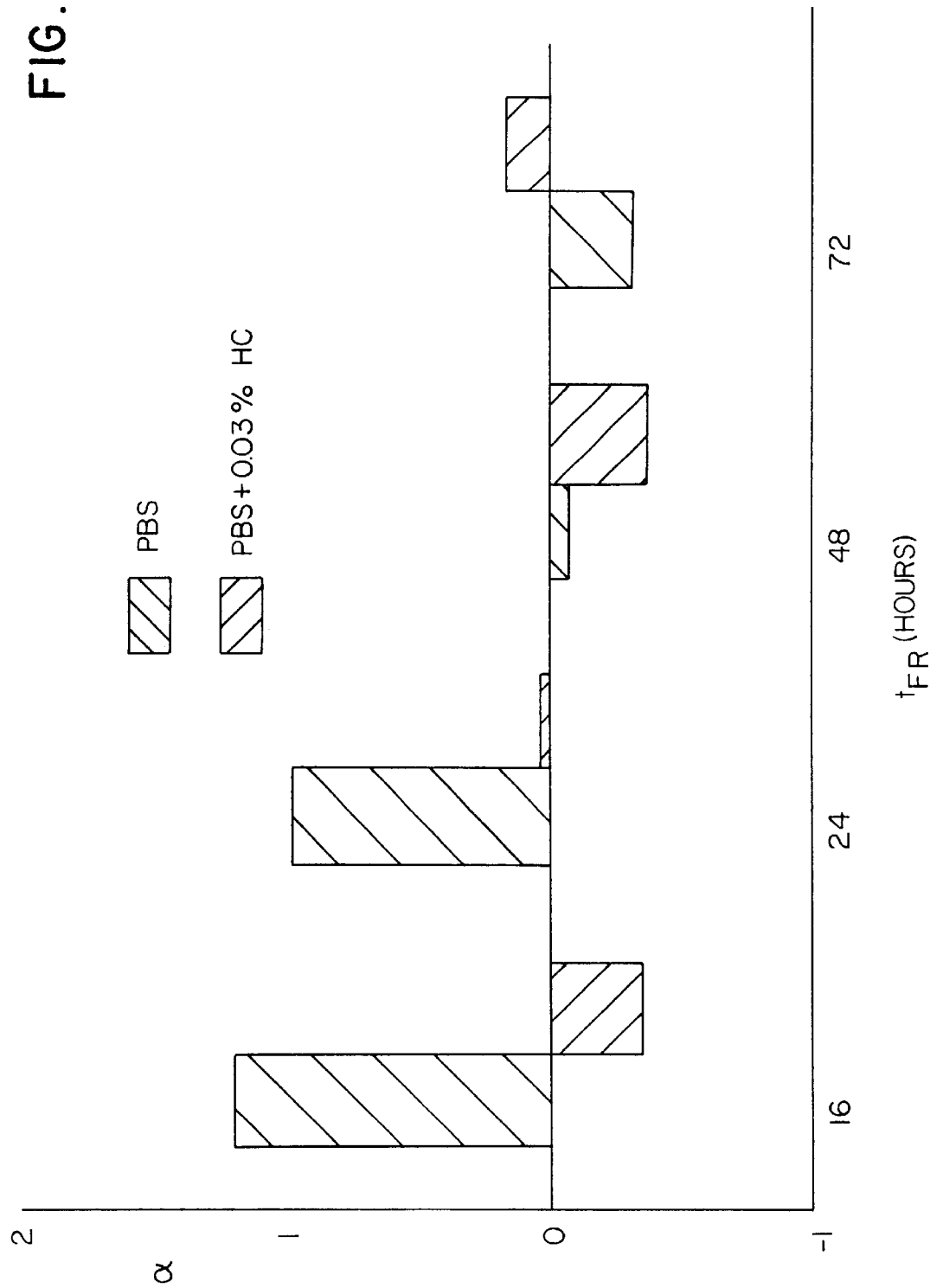
FIG. 5 is a graph of skin irritation ($\alpha$) at the skin site adjacent the cathodic (counter) reservoir as a function of time ($t_w$) during which the electrotransport systems were worn on the skin.

Irritation ($\alpha$) values of the skin sites adjacent to the anodic donor reservoirs are plotted versus time following removal of the electrotransport systems in FIG. 4. Irritation ($\alpha$) values of the skin sites in contact with the cathodic counter reservoirs are plotted versus time following removal of the electrotransport system in FIG. 5.

EXAMPLE III

In vivo electrically assisted delivery of metoclopramide (MCP) was accomplished with the same electrotransport systems used in Example II except the anodic MCP-containing gels contained hydrocortisone (HC) at 0.05 or 0.25 wt % loadings and the cathodic reservoir gels all contained no HC.

Figure 6:
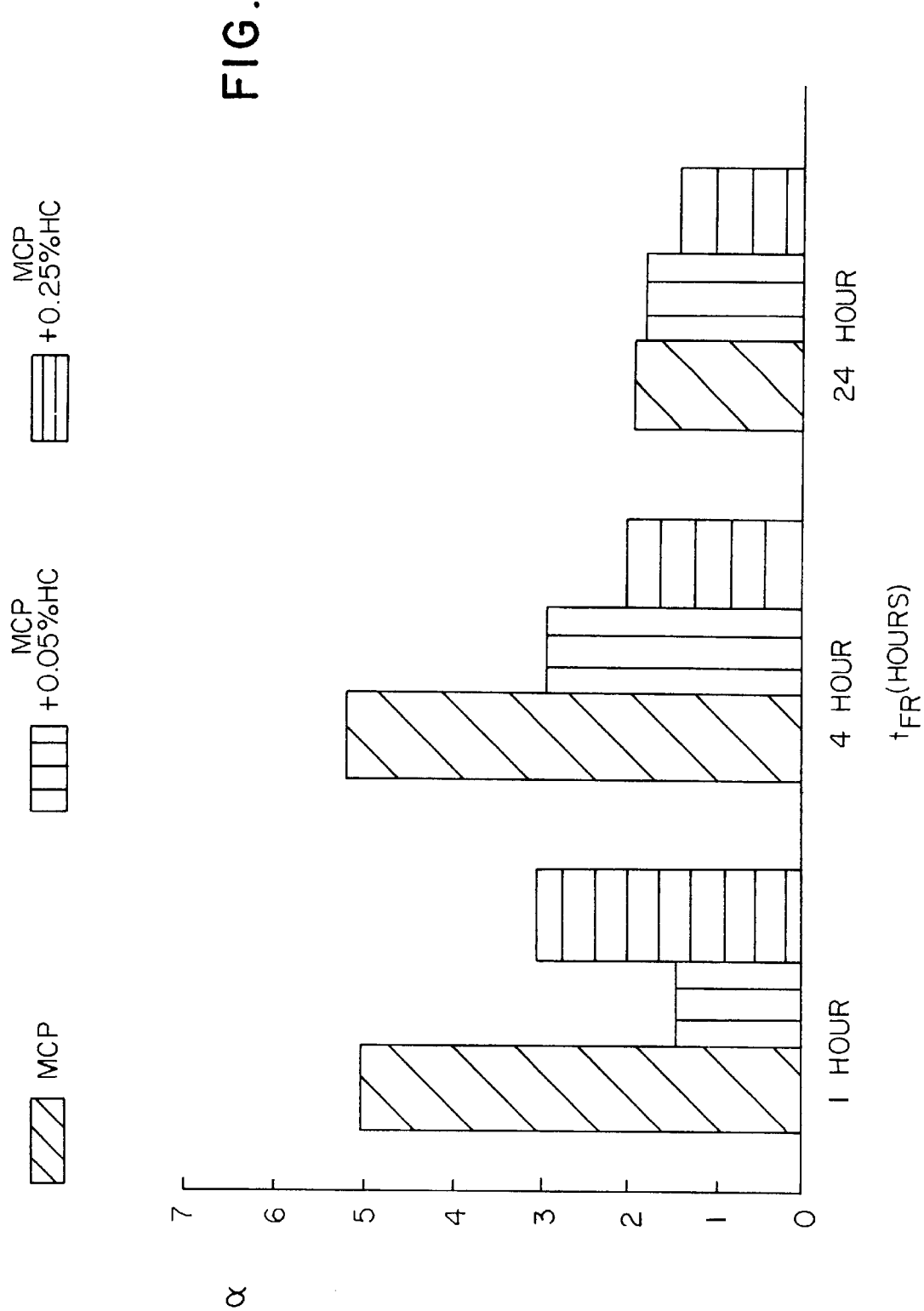
FIG. 6 is a graph of skin irritation ($\alpha$) at the skin site adjacent the anodic (donor) reservoir as a function of time ($t_{FR}$) following removal of the electrotransport systems from the skin.

Six normal male volunteers between 20 and 46 years of age participated in this study. The skin was cleansed with alcohol prior to system application. Each subject wore three electrotransport systems. The anode reservoirs of the three types of electrotransport systems worn by each of the subjects contained MCP alone, MCP with 0.05% HC and MCP with 0.25% HC. The cathode reservoirs of all of the systems contained saline gel. The systems were worn for four hours. Voltage and current were measured just prior to system removal. Skin site evaluations were conducted at 1, 4, 24 and 48 hours following system removal using a Minolta Chroma Meter as described in Example I. FIG. 6 illustrates a plot of the skin irritation ($\alpha$) as a function of time following system removal from the skin.

EXAMPLE IV

In vivo electrically assisted delivery of a placebo drug (sodium chloride) with various liquid solvents was accomplished both with and without co-delivery of an anti-inflammatory agent (hydrocortisone) using electrotransport systems substantially similar to those described in Example II. Four different electrotransport system configurations were constructed. In each of the four electrotransport system configurations, the anodic electrode assembly had a reservoir gel containing a 1.17 mg/mL NaCl (aqueous) solution and 3% hydroxypropyl cellulose (HPC) to form a gel. Each of the four electrotransport systems had a different cathodic reservoir gel. The cathodic reservoir gels were aqueous based solutions containing the materials listed in Table 1.

TABLE 1

| System Number | Cathodic Resevoir |
| --- | --- |
| 1 | 1.17 mg/mL NaCl |
|   | 5 mg/mL Hydrocortisone |
|   | 40% ethanol |
| 2 | 1.17 mg/mL NaCl |
|   | 40 ethanol |
| 3 | 1.17 mg/mL NaCl |
|   | 0.25 mg/mL Hydrocortisone |
| 4 | 1.17 mg/mL NaCl |

The anode material used in each of the systems was silver foil and the cathode material used in each of the systems was silver chloride. The size of the gels and the applied current levels were the same as in Example II.

Figure 7:
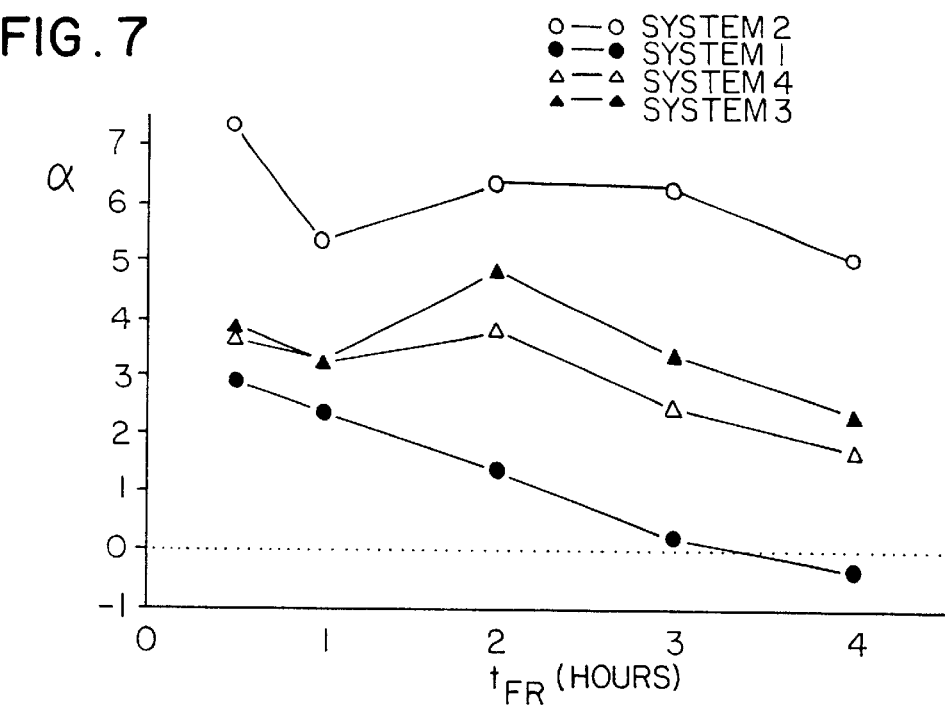
FIG. 7 is a graph of skin irritation ($\alpha$) at the skin site adjacent the cathodic reservoir as a function of time ($t_{FR}$) following removal of the electrotransport systems from the skin.

Irritation ($\alpha$) values of the skin sites adjacent to the cathodic reservoirs are plotted versus wearing time following the removal of the electrotransport systems in FIG. 7. FIG. 7 clearly shows that the cathodic reservoirs containing 40% ethanol and no hydrocortisone caused moderate to severe erythema of the skin. In contrast, the addition of 5 mg/mL hydrocortisone to the ethanol-containing cathodic reservoir (i.e., system 1) resulted in a significant reduction in the reddening of the skin in contact with the cathodic reservoir.

For Systems 3 and 4, both of which contained no ethanol, the erythema values were substantially the same (i.e., at most only about one $\alpha$unit apart) indicating that the hydrocortisone flux from System 3 was not high enough to reduce skin redness. One of the reasons for this is that hydrocortisone is an uncharged species and the electroosmotic flux of hydrocortisone from a cathodic reservoir is substantially lower than from an otherwise equivalent anodic reservoir. Thus, while the 0.25 mg/mL loadings of hydrocortisone in water were insufficient to reduce erythema of the skin in contact with the cathodic reservoir, it is expected that this concentration of hydrocortisone would be sufficient to reduce erythema of the skin in contact with the anodic reservoir.

EXAMPLE V

In vivo electrically assisted delivery of a placebo drug (sodium chloride), with a liquid solvent in which hydrocortisone has good solubility, was accomplished both with and without co-delivery of hydrocortisone using electrotransport systems substantially similar to those described in Example II, and having anodic/cathodic reservoir gels of the following formulations:

| I. | propylene glycol: | 50% (v/v) |
|---|---|---|
| | NaCl: | 0.9% (w/v) |
| | hydroxypropyl methyl cellulose: (Methocell K15 M sold by Dow Chemical Co. of Midland, MI) | 3% (w/v) |
| | water: | (balance) |
| II. | propylene glycol: | 50% (v/v) |
| | NaCl: | 0.9% (w/v) |
| | hydroxypropyl methyl cellulose: | 3% (w/v) |
| | hydrocortisone: | 0.5% (w/v) |
| | water: | (balance) |

An electrotransport system was constructed having anodic and cathodic reservoirs comprised of 350 µl of gel formulation I. This system was applied on the left forearm of a human volunteer. The skin contact area of each electrode gel was 2 cm². The anode material used in the systems was silver foil and the cathode material used in each of the systems was silver chloride. The electrodes were connected to a galvanostat preset to deliver a constant current of 100 µA/cm². Simultaneously another electrotransport system with similar size and current density, but whose anodic and cathodic reservoirs were comprised of 350 µl of gel formulation II was applied on the right forearm of the same volunteer. The systems were worn for 3 hours. After removal, skin irritation ($\alpha$) was monitored using the Minolta Chroma Meter.

Figure 8:
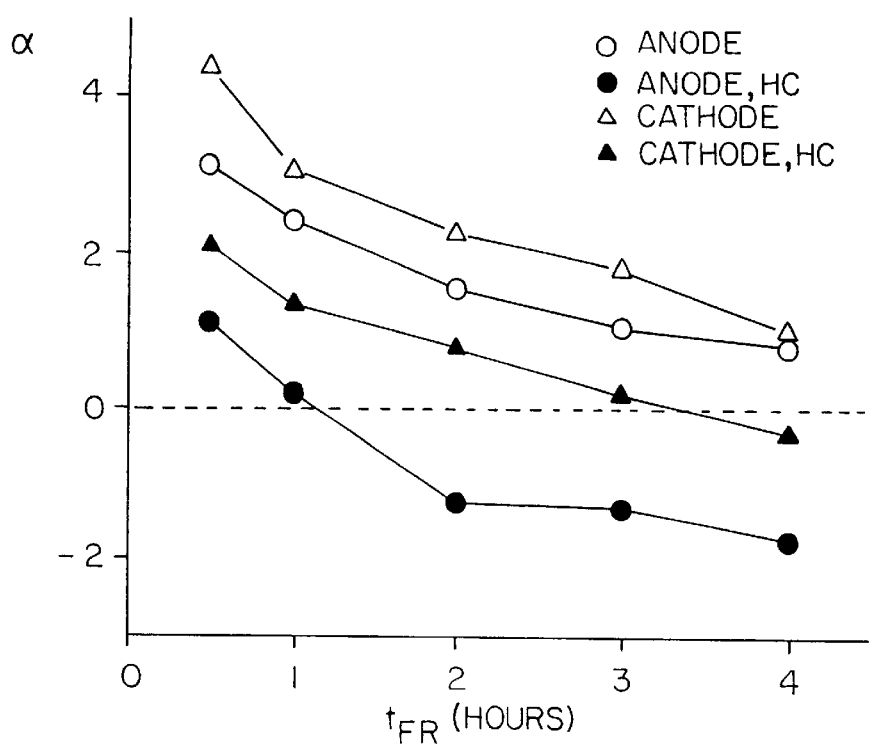
FIG. 8 is a graph of skin irritation ($\alpha$) at the skin sites adjacent the anodic and cathodic reservoirs as a function of time ($t_{FR}$) following removal of the electrotransport systems from the skin.

Irritation ($\alpha$) values of the skin sites in contact with the anodic and cathodic reservoirs of both systems were measured and plotted versus time following the removal of the electrotransport systems in FIG. 8. FIG. 8 clearly shows that both the cathodic and anodic reservoirs containing hydrocortisone (HC) caused substantially less erythema compared to the reservoirs containing no hydrocortisone.

In addition to ethanol, other materials for improving the solubility of hydrocortisone in aqueous solutions include other alcohols such as isopropanol, glycols such as polyethylene glycol and propylene glycol, surfactants such as the TWEEN® class of surfactants and cyclodextrins. Mar. 1, 1994.

Having thus generally described the invention and described in detail certain preferred embodiments thereof, it will be readily apparent that various modifications to the invention may be made by workers skilled in the art without departing from the scope of this invention, which is limited only by the following claims.

What is claimed is:

1. An electrotransport donor reservoir composition, comprising:
   a therapeutic amount of an ionized drug and a skin irritation-reducing amount of an uncharged anti-inflammatory agent, wherein the drug and anti-inflammatory agent are different from one another, the drug and the anti-inflammatory agent being dissolved in a liquid solvent comprising water and a material selected from the group consisting of alcohols, glycols, glycerols, cyclodextrins, non-ionic surfactants and mixtures thereof.

2. The composition of claim 1, wherein the anti-inflammatory agent is selected from the group consisting of hydrocortisone and uncharged esters of hydrocortisone.

3. The composition of claim 1, wherein the solution comprises about 0.1 to 50 mg/ml anti-inflammatory agent.

4. The composition of claim 1, wherein the solution comprises about 3 to 10 mg/ml anti-inflammatory agent.

5. The composition of claim 1, wherein the anti-inflammatory agent is hydrocortisone.

6. The composition of claim 1, wherein the alcohol is selected from the group consisting of ethanol, propanol and isopropanol.

7. The composition of claim 1, wherein the glycol is selected from the group consisting of propylene glycol and polyethylene glycol.

8. The composition of claim 1, wherein the cyclodextrin is selected from the group consisting of $\alpha$, $\beta$, and $\gamma$ cyclodextrins, and anionic and cationic derivatives of cyclodextrin.

9. The composition of claim 1, wherein the skin irritation-reducing amount is an amount which is sufficient to reduce irritation at the site of administration to a level lower than occurs under administration conditions otherwise identical but for the absence of the anti-inflammatory agent.

10. The composition of claim 1, further comprising a hydrophilic polymer.

11. The composition of claim 10, further comprising a hydrophobic polymer.

12. The composition of claim 1, in an anodic reservoir.

13. The composition of claim 1, in a cathodic reservoir.

14. A method of making an electrotransport donor reservoir comprising:
   forming a solution of a therapeutically effective amount of an ionized drug and a skin irritation-reducing amount of an uncharged anti-inflammatory agent, wherein the drug and anti-inflammatory agent are different from one another, by dissolving the drug and the anti-inflammatory agent in a liquid solvent comprising water and a material selected from the group consisting of alcohols, glycols, glycerols, cyclodextrins, non-ionic surfactants and mixtures thereof, and
   adding said solution to a polymeric matrix to form said reservoir.

15. The method of claim 14, wherein the matrix comprises a hydrophilic polymer.

16. The composition of claim 14, wherein the anti-inflammatory agent is hydrocortisone.

17. The method of claim 14, wherein the solution comprises about 0.1 to 50 mg/ml anti-inflammatory agent.

18. The method of claim 14, wherein the solution comprises about 3 to 10 mg/ml anti-inflammatory agent.

19. The method of claim 14, wherein the anti-inflammatory agent is selected from the group consisting of hydrocortisone, hydrocortisone phosphate and hydrocortisone succinate.

20. The method of claim 14, wherein the alcohol is selected from the group consisting of ethanol, propanol and isopropanol.

21. The method of claim 14, wherein the glycol is selected from the group consisting of propylene glycol and polyethylene glycol.

22. The method of claim 14, wherein the cyclodextrin is selected from the group consisting of $\alpha$, $\beta$, and $\gamma$ cyclodextrins, and anionic and cationic derivatives of cyclodextrin.

23. The method of claim 14, wherein the skin irritation-reducing amount is an amount which is sufficient to reduce irritation at the site of administration to a level lower than occurs under administration conditions otherwise identical but for the absence of the anti-inflammatory agent.

* * * * *